United States Patent [19]

Wu

[11] Patent Number: 5,261,392
[45] Date of Patent: Nov. 16, 1993

[54] LARYNGOSCOPE WITH INTERCHANGEABLE FIBEROPTIC ASSEMBLY

[75] Inventor: Tzu-Lang Wu, Fremont, Calif.

[73] Assignee: Achi Corporation, Fremont, Calif.

[21] Appl. No.: 863,117

[22] Filed: Apr. 3, 1992

[51] Int. Cl.⁵ .............................. A61B 1/26
[52] U.S. Cl. ...................... 128/11; 128/200.26
[58] Field of Search .......... 128/11, 200.26, 206.28, 128/206.29, 10, 13, 207.29, 207.14, 634

[56] References Cited

U.S. PATENT DOCUMENTS

| | | | |
|---|---|---|---|
| 3,598,113 | 8/1971 | Moore | 128/11 |
| 4,126,127 | 11/1978 | May | 128/11 |
| 4,306,547 | 12/1981 | Lowell | 128/200.26 X |
| 4,982,729 | 1/1991 | Wu | |

Primary Examiner—Robert Bahr
Assistant Examiner—Beverly A. Meindl
Attorney, Agent, or Firm—Glen R. Grunewald

[57] ABSTRACT

A laryngoscope comprised of an integral handle and curved blade with a bivalve element to form an enclosed passageway with the curved blade, the handle shaped to receive a fiberoptic bundle assembly and the interior of the curved blade having a channel into which a fiberoptic bundle assembly may be placed, with the distal end of said channel forming a circumference for containing the distal end of the fiberoptic bundle assembly.

2 Claims, 3 Drawing Sheets

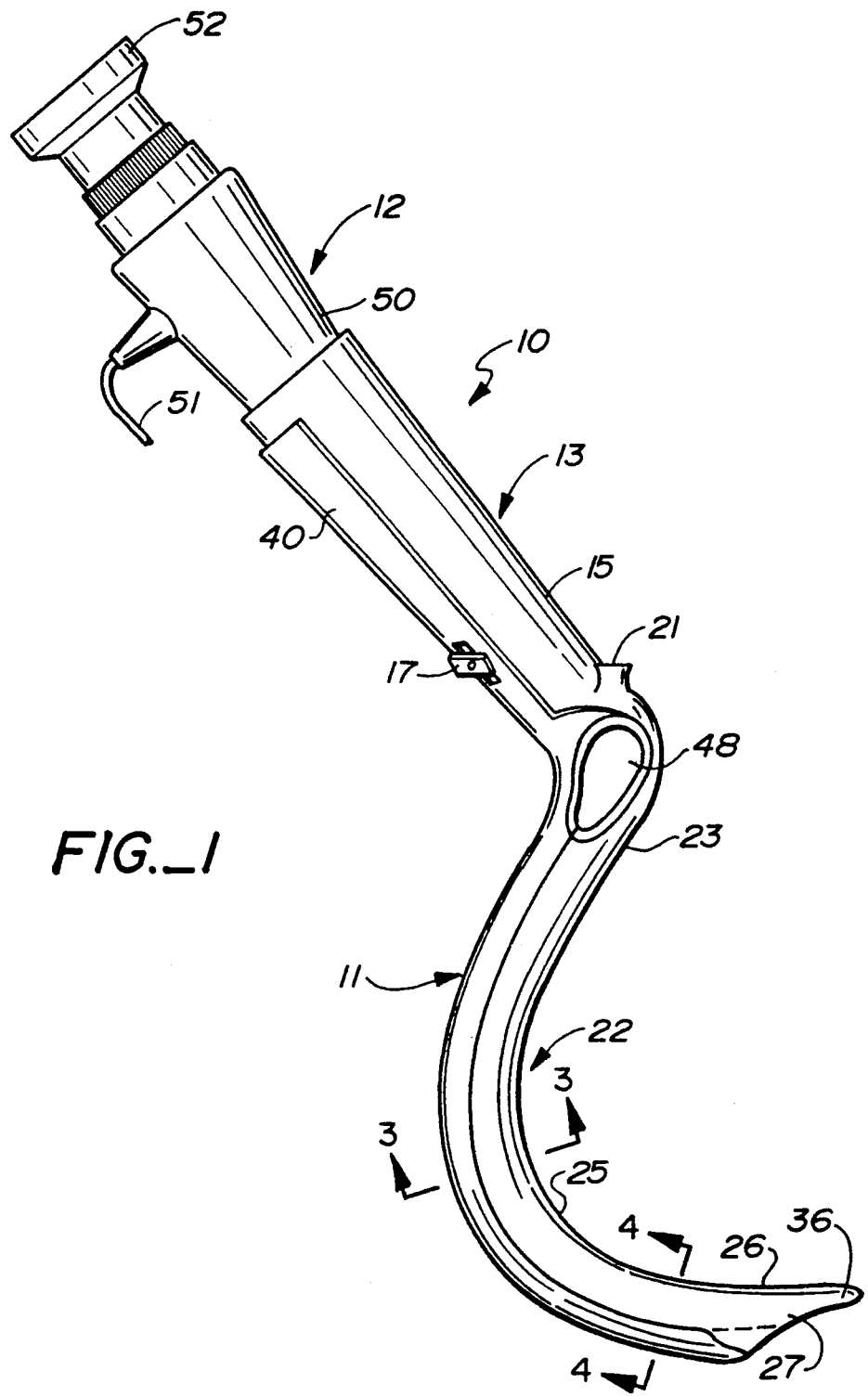
FIG._1

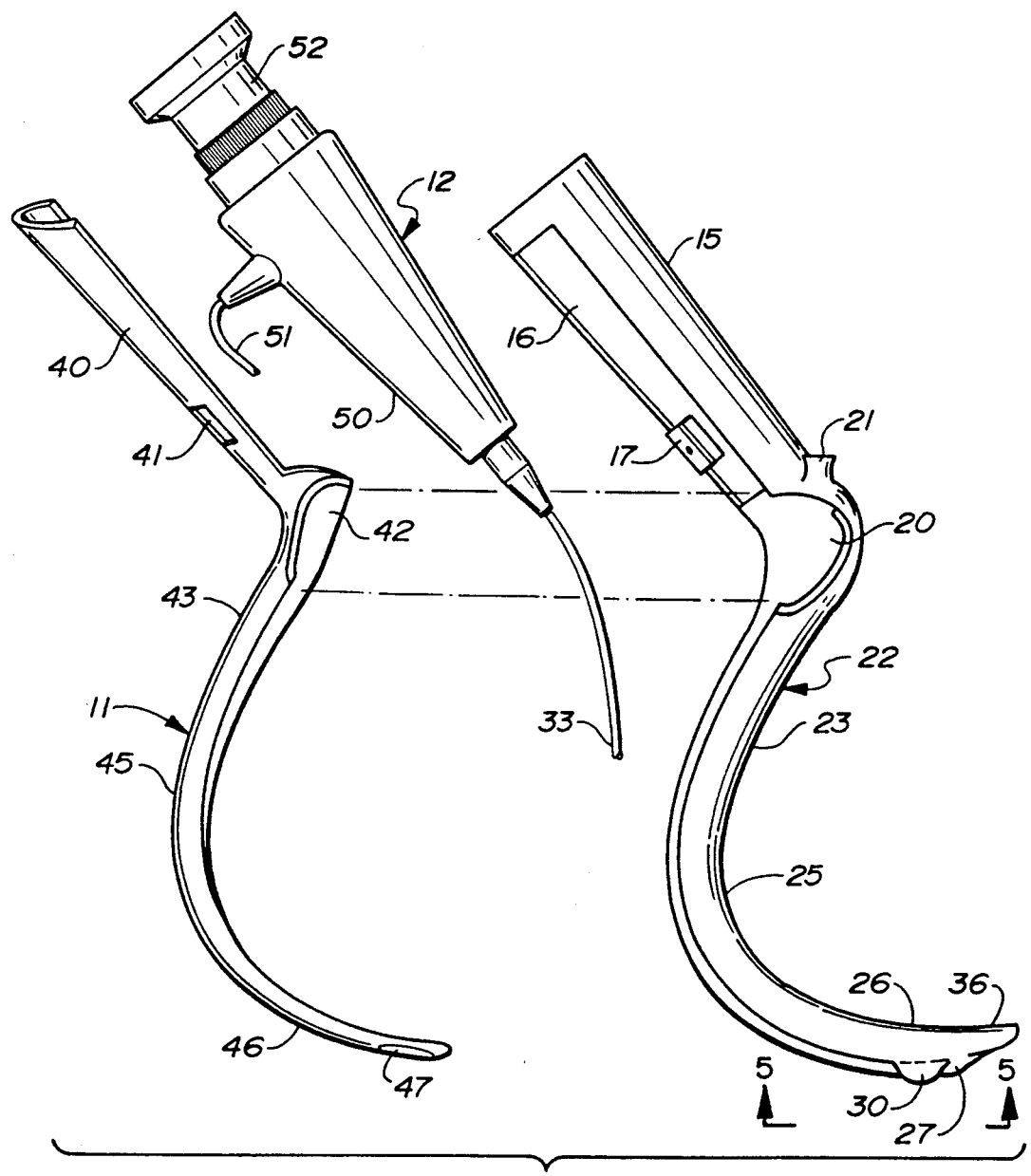
FIG._2

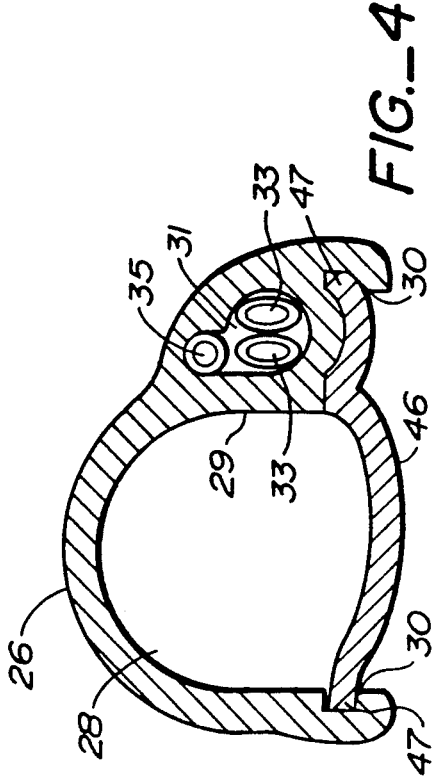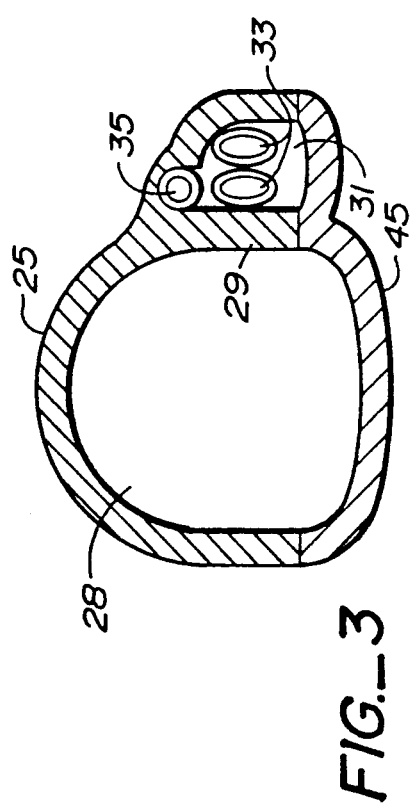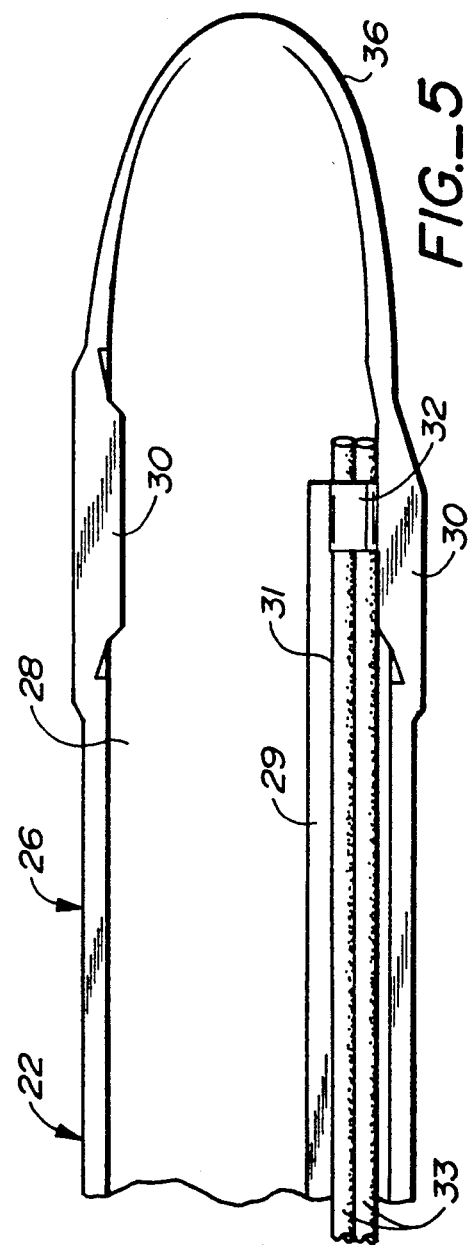

LARYNGOSCOPE WITH INTERCHANGEABLE FIBEROPTIC ASSEMBLY

FIELD OF THE INVENTION

This invention is in the field of medical instruments, particularly laryngoscopes used to intubate patients.

BACKGROUND ART

A laryngoscope is used by a medical professional for procedures that require access to a patient's larynx. One such procedure is intubating the trachea in order to assist or restore a patient's ability to breath. Intubation is performed during surgery, and the ability to intubate a patient rapidly in an emergency is very important.

A conventional laryngoscope has substantially a straight blade. When using a straight-blade laryngoscope to assist in an intubation procedure a physician must insert the laryngoscope blade so that the upper front teeth, the base of the tongue and the larynx of the patient are in a straight line. Only then can the physician directly see the larynx through which intubation is effected. Many patients have low mobility in the head and neck region while others have anatomical variations that prevent a straight line alignment of the upper front teeth, tongue base and larynx and intubating such patients is very difficult because the larynx cannot be seen.

Laryngoscopes fitted with fiberoptic bundles are known. Such laryngoscopes permit a physician to view the larynx even in difficult alignment situations. However, even when a patient's larynx is visible it is sometimes difficult to align the flexible endotracheal tube with the larynx opening and to insert the flexible tube through the larynx. Sometimes a stylet or forceps must be used to guide the tube and the use of such instruments frequently causes injury to the patient.

U.S. Pat. No. 4,982,729 issued to Tzu-Lang Wu discloses a laryngoscope that is a great improvement over the laryngoscopes described above. The laryngoscope of the Wu patent includes a curved blade attached to a handle at a convenient angle, the curved blade comprising two parts connected in bivalve fashion to be assembled before insertion into the patient's mouth. The interconnected bivalve elements can be disconnected within the patient's throat after intubation has been effected so that the laryngoscope can be removed from the patient in two pieces leaving the endotracheal tube in place. The laryngoscope of the Wu patent may or may not have fiberoptic bundles to provide light and a view of the area of the patient's larynx, and when such bundles are used they must be permanently connected to the blade of the laryngoscope. Accordingly, each laryngoscope blade must have its own dedicated fiberoptic bundles, and fiberoptic bundles are by far the most expensive element of a laryngoscope.

Each facility using a laryngoscope must have a number of blades available in different sizes. A large adult takes a different size blade than a small adult takes, and pediatric sized laryngoscope blades cannot be used for adult patients. The fiberoptic bundles used with the laryngoscopes disclosed in the Wu patent occupy space within the laryngoscope blade in the vertical direction which clutters the interior of the laryngoscope, thus requiring greater vertical dimension in order to pass an endotracheal tube through the laryngoscope. The vertical dimension of a laryngoscope blade is most critical and desirably it is as small as possible.

Fiberoptic bundles should be positioned so that loose tissue or an unduly relaxed epiglottis cannot block the light provided by a fiberoptic bundle or obscure the user's view of a patient's larynx.

DISCLOSURE OF THE INVENTION

This invention is a laryngoscope of the curved, bivalve blade type disclosed in Wu patent No. 4,982,729 but it is constructed to overcome the problems noted above. The laryngoscope of this invention will accept an interchangeable fiberoptic bundle set having both illuminating fibers and viewing fibers so that a single fiberoptic set may be used interchangeably with many different laryngoscopes embodying this invention, even if those laryngoscopes have different sized blades. A fiberoptic bundle is accepted in an interior channel within the laryngoscope blade which holds it firmly in place but it is removable from the channel so that it may be cleaned and sterilized after which it may be used in other laryngoscopes. The channel for holding the fiberoptic bundle is positioned in the laryngoscope blade end to be remote from the position of the epiglottis or other loose tissue in the region of the larynx thereby avoiding blocking of light or obscuring the view of an operator.

The laryngoscope of this invention additionally includes a permanent channel to hold an oxygen tube. The oxygen tube is positioned to discharge in the vicinity of the end of the fiberoptic bundle which both oxygenates the viewing area and provides a flowing gas stream which prevents fogging of the fiber ends of the viewing fiberoptic bundle. The fiberoptic bundle and the oxygen tube are in grooves or channels located close to the abutting edges of the blade and bivalve element which is along the side of the endotracheal tube channel within the laryngoscope. In that location the fiberoptic bundle and oxygen tube occupy none of the critical vertical space in the laryngoscope thereby permitting the scope to have a shorter vertical dimension which makes it correspondingly easier to use. The oxygen tube may be permanently fixed in the laryngoscope blade of this invention, being welded in place, and it may be much smaller in diameter than the fiberoptic bundles.

BRIEF DESCRIPTION OF THE DRAWINGS

FIG. 1 is a side view of a laryngoscope embodying this invention.

FIG. 2 is an exploded perspective view of the laryngoscope illustrated in FIG. 1.

FIG. 3 is a cross section taken along the line 3—3 of the laryngoscope illustrated in FIG. 1.

FIG. 4 is a cross section taken along the line 4—4 of the laryngoscope illustrated in FIG. 1.

FIG. 5 is a partial bottom plan view of the region 5—5 of the laryngoscope illustrated in FIG. 2.

BEST MODE FOR CARRYING OUT THE INVENTION

FIG. 1 illustrates a laryngoscope generally designated 10 embodying this invention. The laryngoscope of FIG. 1 is assembled for use. It includes a bivalve part 11, a fiberoptic part 12, and a blade part 13. The blade part 13 includes a conical handle or at least a handle having a conical cavity in it to receive the fiberoptic part 12. The handle 15 includes a recess 16 (FIG. 2) to receive a corresponding flange 40 of the bivalve element 11 as will be shown below. The recess 16 is provided with a latch 17. The handle 15 is connected to a blade generally designated 22 and where handle 15 meets blade 22 an opening segment 20 is provided.

The blade 22 is connected to handle 15 at the blade straight portion 23 and it blends into a curved portion 25 which in turn blends into a straight terminal portion 26. The terminal portion 26 terminates in an open end 27.

The blade 22 is curved in cross section so that it forms a channel 28 which becomes a closed passageway when positioned against the bivalve part 11. A wall 29 separates internal groove 31 from 28. At the distal end of the blade 22 an interlock element 30 is formed on each side, and they are positioned to embrace the end of bivalve element 11 when it is in place, as explained below. A holding collar 32 encloses the end of internal channel 31 to surround the ends of fiberoptic bundles 33 to hold those ends in place as will be described below. The internal groove 31 contains an oxygen tube 35 which in this embodiment is fixed within that groove 31 and arranged so that its open end discharges through open end 27 of the blade and its other end is connected to oxygen inlet 21. The end of the blade is in the form of a tapered tip 36 which provides a thin leading edge for insertion in a patient's throat.

Bivalve element 11 includes a handle-engaging flange which also contains a latch opening 41. At the intersection of flange 40 and the blade-engaging straight portion 43, the bivalve portion is provided with a tube-opening segment 42. When tube-opening segment 42 and tube-opening segment 20 are placed together they form an opening 48 shown in FIG. 1. A blade engaging straight part 43 is shaped to correspond to the shape of straight portion 23 of blade 22. Portions 45 and 46 of the bivalve element are shaped to correspond with portions 25 and 26 respectively of the blade 22.

The fiberoptic part 12 includes a tapered conical insert 50 that tapers the same as a conical cavity in handle 15. The fiberoptic part 12 has two fiberoptic bundles, one for illumination and one for viewing. A light source, not shown, is within fiberoptic part 12 and aligned with the ends of the fibers in the illuminating bundle, as is known in the art, and power for that illumination source is provided through wire 51. An eye piece 52 is connected to view the image from the viewing fiberoptic bundle to provide visibility of the region near the end of the laryngoscope to an operator. Fiberoptic bundles 33 are shown extending from the bottom of element 12 in FIG. 2.

To use the laryngoscope of this invention the tapered insert 50 is inserted into handle 15 and the fiberoptic bundles 33 are threaded into the blade 22. The ends of the fiberoptic bundles are inserted beneath collar 32 and the remainder of the fiberoptic bundles are wedged into the internal groove 31 behind the wall 29 so that the bundles 33 are within internal groove 31 and held frictionally so that they cannot readily be dislodged. As best seen in FIG. 3 and FIG. 5 oxygen tube 35 is permanently fixed and need not be inserted. With the ends of fiberoptic bundles placed beneath collar 32, the ends of the fiberoptic bundles are at the desired position to best illuminate and view the region of the larynx for an operator. When the fiberoptic bundles are in place the bivalve element is ready to be assembled.

To use the laryngoscope of this invention the end 47 of the bivalve part 11 is inserted into the interlock elements 30 on the end of blade 22 and then the remainder of the bivalve element is brought into contact with the blade 15 so that flange 40 lies in recess 16 and latch 17 extends through latch opening 41. When the latch is locked the bivalve element and the blade are held in firm engagement to act as one piece and form a passageway in which the fiberoptic bundles are contained behind the wall 29. When the bivalve element and the blade are interlocked together an endotracheal tube, not shown, is threaded into opening 48 and through the passageway formed by the blade and the bivalve element until the end of the endotracheal tube is just short of the end 27. An oxygen source may be connected at inlet 21 and the laryngoscope of this invention is then inserted into a patient's mouth and maneuvered until the end 36 is closely in front of a patient's larynx. Maneuvering the end of the laryngoscope is easily accomplished because the operator has a view of the larynx provided by illumination through one fiberoptic bundle and viewing through another fiberoptic bundle. At that point the endotracheal tube may be slid further through the laryngoscope and it easily passes through the larynx of the patient to provide air or oxygen to the patient's trachea.

When the larynx of a patient is intubated the latch 17 is released, the bivalve element 11 is drawn away from the blade element so that the interlock between the end of the bivalve element 11 and interlock elements 30 is released, and the bivalve element and laryngoscope blade can then be independently removed from the patient's mouth leaving the endotracheal tube in place. The ends of the fiberoptic bundles are not covered by the endotracheal tube nor by soft tissue in the are of the larynx because they are held to one side in an area protected by the blade. In addition, the operator knows the location of the ends of the fiberoptic bundles within the blade and can maneuver the blade to give illumination and a view of the desired area. The entire intubation can be carried out very quickly which is important in emergency situations, particularly where there is edema in the region of a patient's larynx.

When the laryngoscope is removed from the patient in two pieces the fiberoptic portion can readily be removed from the blade element. The blade element, the bivalve element and the fiberoptic part can be independently sterilized. The fiberoptic bundle element can then be returned to inventory to be used again with the same or with a different laryngoscope. By virtue of this invention a medical facility may have a large inventory of laryngoscopes of different sizes and shapes to be used with large patients, small patients, or children of various ages but only a very few of the expensive fiberoptic bundles need be maintained in that they can be used interchangeably with different laryngoscopes.

I claim:

1. In a laryngoscope having a handle attachable to a fiberoptic bundle assembly, a curved blade connected to said handle, said curved blade having interlocking means at the distal end thereof for connecting it to a bivalve element and with said interconnected blade and bivalve element having abutting edges and forming an enclosed passageway, the improvement comprising:
   a wall positioned within said blade so as to form an open channel within said passageway adjacent an abutting edge of said blade, said open channel having dimensions to contain a fiberoptic bundle assembly, said open channel terminating in a circumferentially enclosed region to enclose and maintain the position of the distal end of said fiberoptic bundle assembly in the proximity of the distal end of said blade, whereby when said bi-valve element is positioned against and interconnected with said blade, said open channel becomes an enclosed channel;

a permanent oxygen passageway affixed within said open channel and opening at one end substantially at the distal end of said blade;

means in said handle for passing a fiberoptic bundle assembly through said handle to extend through said open channel to the distal end of said blade.

2. The laryngoscope of claim 1 wherein said fiberoptic bundle assembly includes a conical portion, said handle includes a conical cavity shaped to receive said conical portion of said fiberoptic assembly.

* * * * *